United States Patent [19]

Ogawa

[11] Patent Number: 4,680,445

[45] Date of Patent: Jul. 14, 1987

[54] ELECTRONICALLY-CONTROLLED HEATING DEVICE FOR INFUSION LIQUIDS

[76] Inventor: Genshiro Ogawa, 13-3, Oaza Inuyama Aza Nishikoken, Inuyama-shi, Aichi-ken, Japan

[21] Appl. No.: 773,020

[22] Filed: Sep. 6, 1985

[30] Foreign Application Priority Data

| Sep. 6, 1984 | [JP] | Japan | 59-187112 |
| Nov. 12, 1984 | [JP] | Japan | 59-238185 |
| Nov. 30, 1984 | [JP] | Japan | 59-182557[U] |
| Jan. 9, 1985 | [JP] | Japan | 60-1185[U] |

[51] Int. Cl.⁴ .................... H05B 1/02; A61F 7/00; B67D 5/62; F24H 1/12
[52] U.S. Cl. ........................ 219/299; 165/46; 219/302; 219/305; 219/308; 219/309; 604/114
[58] Field of Search ............... 219/296, 298, 299, 297, 219/301–305, 308, 309; 604/114, 113; 165/46

[56] References Cited

U.S. PATENT DOCUMENTS

| 3,293,868 | 12/1966 | Gonzalez | 165/46 X |
| 3,443,060 | 5/1969 | Smith | 165/46 X |
| 3,485,245 | 12/1969 | Lahr et al. | 165/46 X |
| 3,590,215 | 6/1971 | Anderson et al. | 219/298 |
| 4,293,762 | 10/1981 | Ogawa | 219/330 X |
| 4,309,592 | 1/1982 | LeBoeuf | 219/330 X |
| 4,314,143 | 2/1982 | Bilstad et al. | 604/114 X |
| 4,356,383 | 10/1982 | Dahlberg et al. | 219/330 X |
| 4,384,578 | 5/1983 | Winkler | 604/114 |
| 4,473,739 | 9/1984 | Scheiewe et al. | 219/302 |
| 4,532,414 | 7/1985 | Shah et al. | 219/302 X |

Primary Examiner—Anthony Bartis
Attorney, Agent, or Firm—Dennison, Meserole, Pollack & Scheiner

[57] ABSTRACT

A device for heating an infusion liquid to be injected into a human body includes a casing having an open top and a closed bottom, with a liquid inlet section and a liquid outlet section, providing a compartment receiving a heating bag providing flow passage for the liquid to be heated. Two heating plates are mounted on the casing bottom and three thermosensors are provided; the first at the inlet section, the second between the heating plates and the third at the outlet section. A cover closing the open top is provided with a push plate holding the bag against the heating plates. A control circuit controls the first heating plate in response to the temperature in the vicinity of the bag inlet and the middle of the bag as detected by the first and second thermosensors and the second heating plate in accordance with the temperature in the vicinity of the bag outlet as detected by the third thermosensor. The control circuit is also responsive to a flow rate detector. The casing orients the heating plates and push plate vertically during use and the push plate and heating plates may be provided with opposed wedged-shaped ridges causing the flow passage in the bag to assume a shape which reduces bubble formation and promotes rapid ejection of any bubble formed.

5 Claims, 14 Drawing Figures

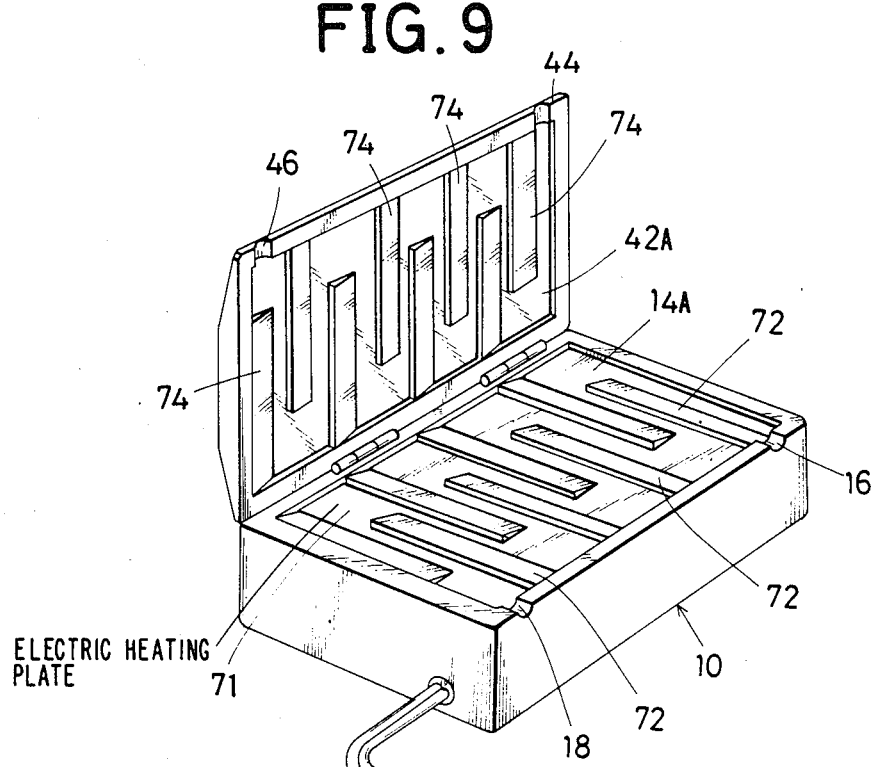
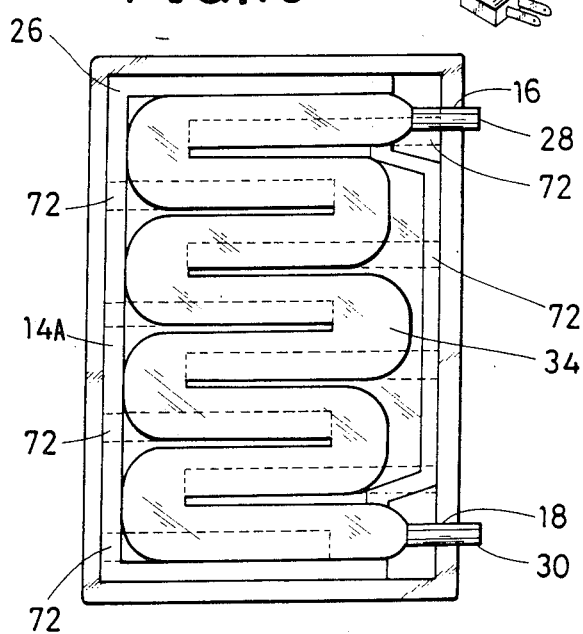

FIG.11
FIG.12
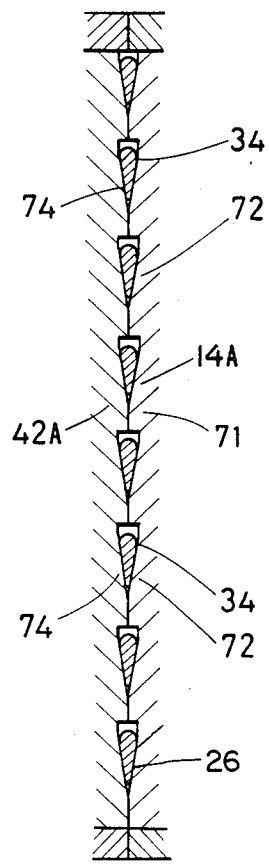
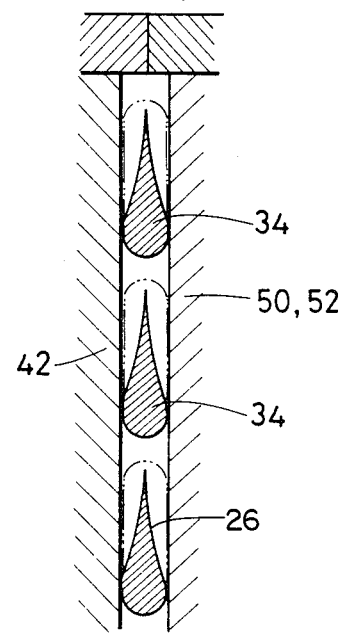

ELECTRONICALLY-CONTROLLED HEATING DEVICE FOR INFUSION LIQUIDS

BACKGROUND OF THE INVENTION

1. Field of the Invention

The present invention relates to a device for heating infusion liquid such as instillation liquid and blood transfusion liquid. More particularly, the invention relates to such device for injecting instillation liquid, blood transfusion liquid and/or other infusion liquid into the body of a patient at an optimum temperature.

2. Description of the Prior Art

Various devices have been devised heretofore to heat infusion liquid such as instillation liquid and blood transfusion liquid. In one known arrangement, a heating plate or heater is disposed in a casing, and a heater activating and associated control means are electrically connected to the heating plate. A liquid tube or heating bag is held between the heating plate and a cover body so that the liquid therein can be heated. In any case, such a heating device is provided at the outlet portion thereof with a thermosensor for detecting the temperature of the liquid heated by the heating device, and in accordance with the results of measurement, the control means is operated to control the heater activating means in such a manner as to adjust the temperature of the liquid. In the heating device described above, however, the heater activating means is controlled in accordance with the temperature of the heated liquid and thus, such control cannot follow variations in the temperature or flow rate of the liquid on the inlet side. This results in failure to accurately control heating of the liquid, causing uneven heating, and thereby failure to supply the liquid heated to a desired temperature.

OBJECTS AND SUMMARY OF THE INVENTION

Accordingly, it is an object of the present invention to provide a novel electronically-controlled device for heating infusion liquid such as instillation liquid and blood transfusion liquid which permits accurate adjustment of temperature of the liquid by controlling heating means in accordance with the temperature of the liquid as it flows into the heating device.

Another object of the present invention is to provide such device which permits accurate heating of the liquid to a desired temperature by controlling heating means in accordance with not only the temperature but also the flow rate of the liquid as it flows into the heating device.

A further object of the present invention is to provide such device in which, while the liquid flowing into the heating device is heated and flows out, generation of bubbles in the liquid is prevented in the heating device.

A still further object of the present invention is to provide such device in which the contacting condition between heating plates and a heating bag in the heating device is improved to achieve better heating efficiency.

According to the present invention, there is provided a device for heating infusion liquid such as instillation liquid and blood transfusion liquid which comprises a casing, a heating bag and an openable cover. The casing has an open top and a closed bottom, with a liquid inlet section and a liquid outlet section, to thereby provide a compartment for storing the heating bag. The openable cover is connected to the casing for covering the whole heating bag storing compartment. The casing also has on the back thereof a circuit element storing compartment accommodating an electic heating circuit and control means and which is closed up tightly by a bottom cover. The heating device is put in operation when connected to an external power supply. The heating bag is a generally flat sealed bag of laminated thin plastic films with its upper and lower ends connected to pipes, and is provided with pectinate partitions extending alternately from either side thereof in a staggered manner. The heating bag is removably mounted to the casing, with the upper and lower ends positioned at the inlet and outlet sections, respectively, of the casing, so that the liquid introduced through the pipe connected to the upper end of the heating bag flows down in a zigzag way in the heating bag. The bottom portion of the heating bag storing compartment has a first heating plate for heating a half part of the liquid on the inlet side and a second heating plate for heating the other half part on the outlet side, and thermosensors are respectively disposed adjacent the inlet section, between the first and second heating plates, and adjacent the outlet section. Temperature signals from these three thermosensors are fed to an electronic control circuit of the control means, and the result of predetermined operations is given as an output for controlling the heating rate of the first and second heating plates.

The present invention will become more fully apparent from the claims and description as it proceeds in connection with the drawings.

BRIEF DESCRIPTION OF THE DRAWINGS

FIG. 9 is a perspective view of the heating device incorporating a further embodiment of the present invention, with its cover open;

FIG. 10 is a top plan view of the embodiment shown in FIG. 9;

FIG. 11 is an enlarged fragmentary sectional view of the embodiment shown in FIG. 9;

FIG. 12 is an enlarged fragmentary sectional view of the heating system of the embodiments shown in FIGS. 1 and 7;

DETAILED DESCRIPTION OF THE PREFERRED EMBODIMENTS

Figure 1:
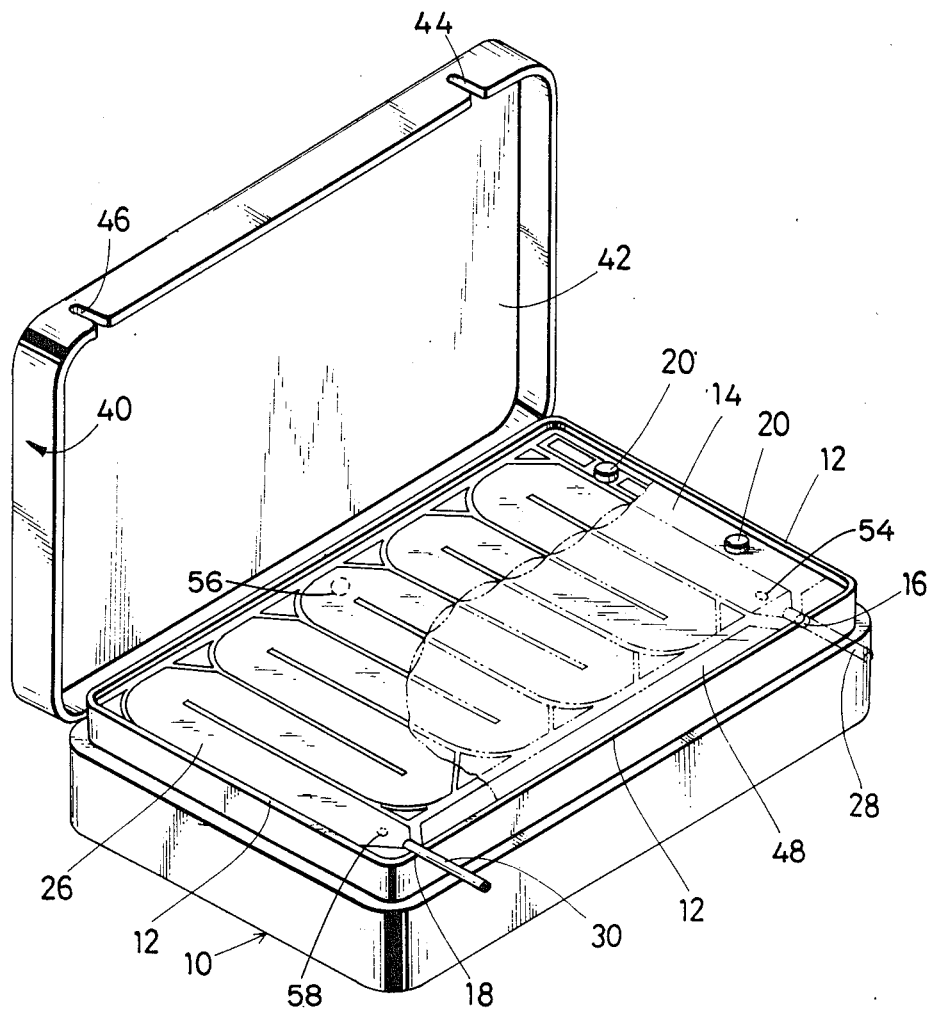
FIG. 1 is a perspective view of a heating device according to an embodiment of the present invention, with its cover open.

Referring now to the drawings and to FIG. 1 in particular, shown therein is a heating device constructed in accordance with the present invention. As shown therein, the device includes a casing 10, a heating bag 26, and a cover 40.

Figure 2:
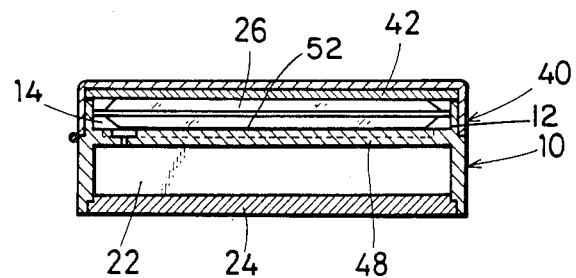
FIG. 2 is a vertical sectional view of the heating device of FIG. 1, with its cover closed.

The casing 10 has along the top periphery thereof a rib 12 of a width substantially equal to the thickness of the heating bag, thereby providing a compartment 14 having an open top for storing the heating bag 26. The rib 12 has a first and a second cutout section 16 and 18 for receiving an inlet pipe 28 and an outlet pipe 30, respectively, for the heating bag 26. Adjacent one end of the heating bag storing compartment 14, the casing 10 is provided with two cylindrical projections 20 for mounting the heating bag 26 thereto. As shown in FIG. 2, the casing 10 has underneath the bottom, indicated at 48, a circuit element storing compartment 22 for accomodating an electric heating circuit and associated control means not shown. These components are sealed by a cover plate 24.

Figure 3:
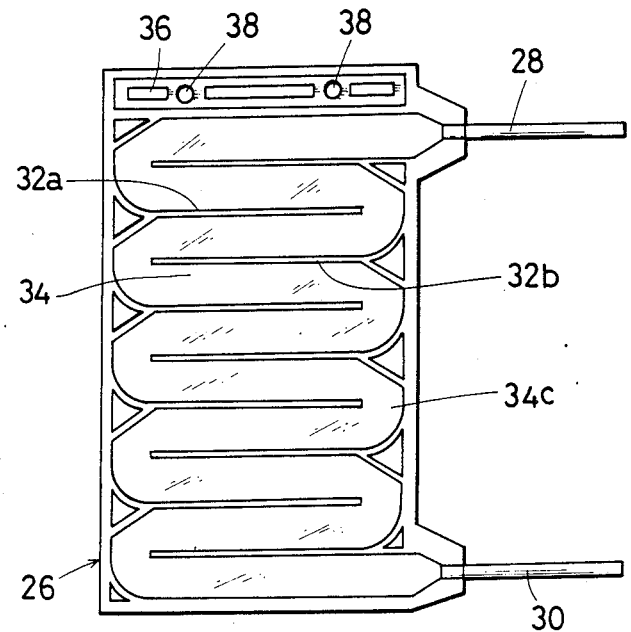
FIG. 3 is a plan view of a heating bag of the embodiment shown in FIG. 1.

As best shown in FIG. 3, the heating bag 26 is a generally flat sealed bag made of laminated thin plastic films which has an upper and a lower end connected to the inlet pipe 28 and the outlet pipe 30, respectively. The heating bag 26 is provided with pectinate partitions 32a and 32b extending alternately from either side thereof in a staggered manner to form a liquid passage 34 with its turning portions 34c in the form of a rounded U-shaped corner. Thus constructed, the liquid fed through the inlet pipe 28 flows down through the passage 34 in the heating bag 26 in a zigzag way and flows out through the outlet pipe 30. The heating bag 26 also is provided on the upper side thereof with a fitting piece 36 having two fitting holes 38 into which the projections 20 of the casing 10 is inserted to mount the same.

Turning to FIGS. 1 and 2, the cover 40 is hinged to one side of the casing 10 to be freely opened and closed relative to the latter. The cover 40 has a push plate 42 resiliently supported on the inside thereof, which is large enough to cover the entire heating bag storing compartment. The cover 40 also has at the edge portion thereof a pair of U-shaped cutout sections 44 and 46 for allowing the inlet pipe 28 and the outlet pipe 30 to pass, when the cover 40 is closed. While not shown, the cover 40 is provided on the top thereof with indicators such as a liquid temperature indicator, a pilot lamp of power supply and an emergency lamp, and a power switch.

Figure 4:
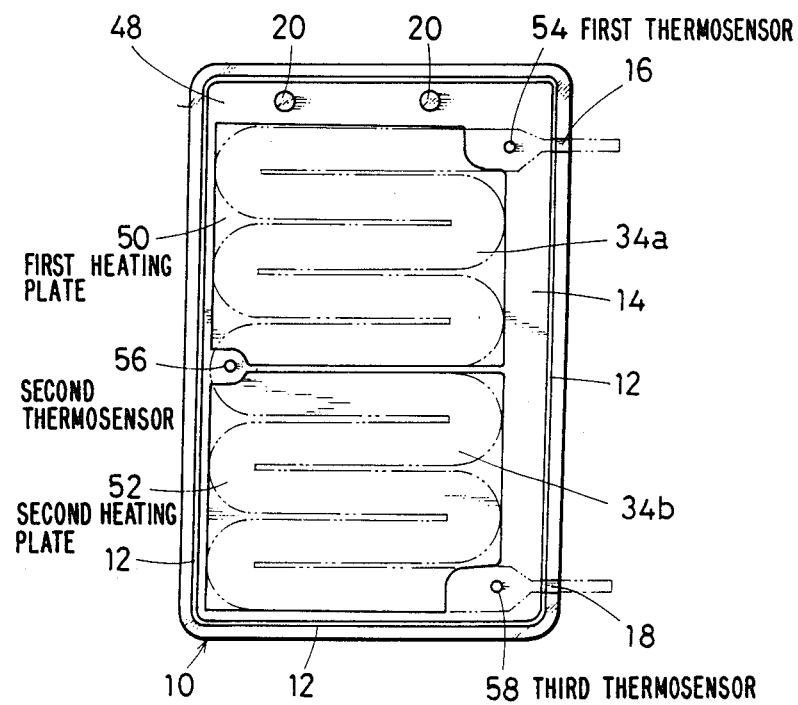
FIG. 4 is a plan view of a heating bag storing compartment of the heating device shown in FIG. 1.

With reference to FIG. 4, the casing 10 includes a first heating plate 50 mounted on the upper half part of the bottom 48 of the heating bag storing compartment 14, which serves to heat a half part 34a of the passage 34 on the inlet side of the heating bag 26; and a second heating plate 52 mounted on the lower half part of the bottom 48, which serves to heat the other half part 34b of the passage 34 on the outlet side of the heating bag 26. The bottom 48 of the casing 10 also is provided with a first thermosensor 54 between the first cutout section 16 and the first heating plate 50, a second thermosensor 56 at a position abutting on the passage 34 between the first and second heating plates 50 and 52, and a third thermosensor 58 between the second cutout section 18 and the second heating plate 52. It is to be noted that the bottom 48 of the casing 10 is made of a heat insulating material, preventing any influence of heat of the heating plates 50 and 52 upon the thermosensors 54, 56 and 58.

When the heating device is used, the casing 10 is supported vertically, that is with the open top in a vertical plane, extending between a source of liquid and a patient. The heating bag 26 is mounted within the storing compartment 14, with the cylindrical projections 20 of the storing compartment 14 inserted into the fitting holes 38. The inlet pipe 28 and the outlet pipe 30 are positioned in the respective cutout sections 16 and 18, and then the cover 40 is closed. At this time, as the inlet pipe 28 and the outlet pipe 30 are also received in the cutout sections 44 and 46 of the cover 40, the pipes 28 and 30 are led out of the heating device to be connected to external liquid pipes, respectively. The heating bag 26 is thus held between the heating plates 50 and 52 provided in the storing compartment 14 and the push plate 42 mounted to the cover 40.

Figure 5:
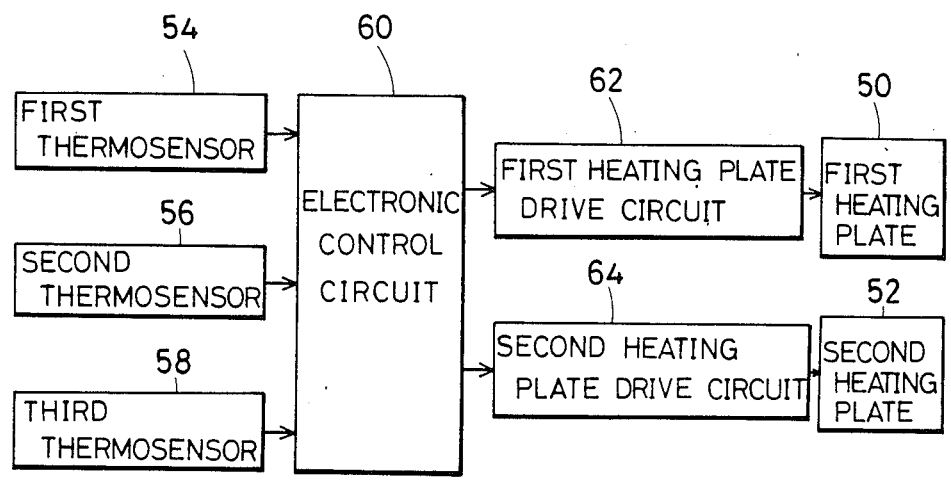
FIG. 5 is a block diagram illustrating the control system for the heating device.

Now, the description will be related to the electric circuit for the above described heating device. FIG. 5 is a block diagram of the circuit and as may be seen, an electronic control circuit 60 is provided serving as heating control means which comprises a read-only memory (ROM) for storing a control program, a random access memory (RAM) for storing various data, etc., and is operated according to the control program. The control circuit 60 receives detected signals from the first, second and third thermosensors 54, 56 and 58, calculates the liquid temperatures $t_1$, $t_2$ and $t_3$ at the respective detecting positions, and in accordance with the temperatures $t_1$, $t_2$ and $t_3$ thus obtained, transmits control signals to a first heating plate driving circuit 62 and a second heating plate driving circuit 64 to control the heating operation of the first and second heating plates 50 and 52, so that the liquid can be heated to be supplied through the outlet pipe 30 of the heating bag 26 at a reference temperature $t_s$ (36° C. in this embodiment) previously stored in the ROM.

Specifically, the control circuit 60 calculates the temperature $t_1$ of the liquid which comes into the heating bag 26 and which is not yet heated in accordance with the detected signal from the first thermosensor 54; the temperature $t_2$ of the liquid flowing in the heating bag 26 after heated by the first heating plate 50 in accordance with the detected signal from the second thermosensor 56; and the temperature $t_3$ of the liquid flowing out of the heating bag 26 after reheated by the second heating plate 52. Then, the control circuit 60 transmits a control signal to the second heating plate driving circuit 64 to control the heating operation of the second heating plate 52, so that the temperature $t_3$ will reach the reference temperature $t_s$ (36° C.), and at the same time, controls the heating operation of the first and second heating plates 50 and 52, so that the temperature $t_1$ of the liquid coming into the heating bag 26 rises at a constant rate as shown by the temperature line L in FIG. 6 until it reaches the reference temperature $t_s$.

Figure 6:
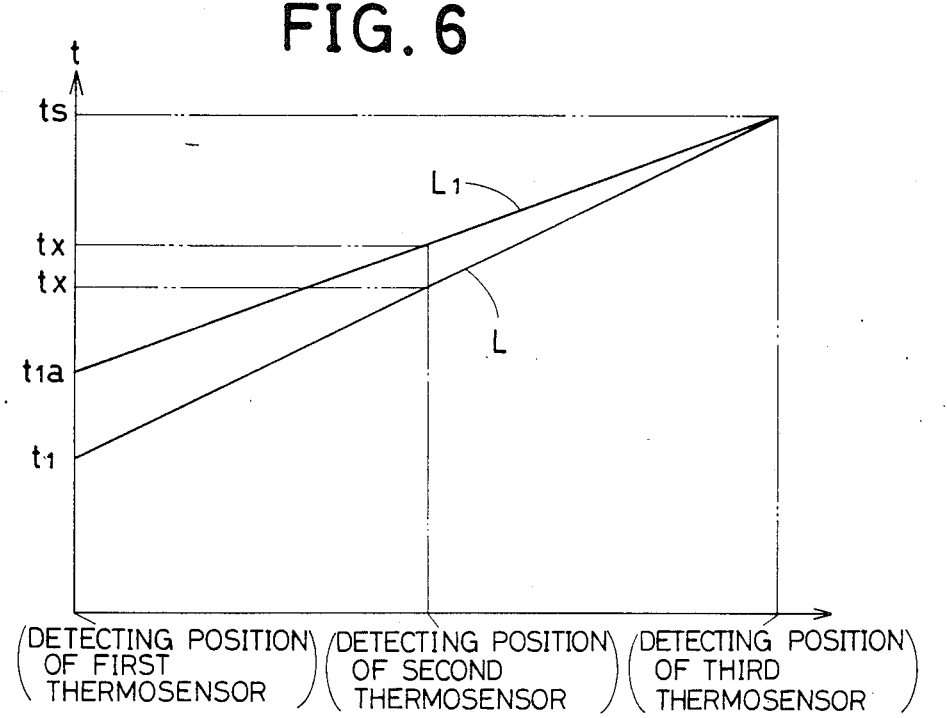
FIG. 6 is an operational diagram illustrating the heating condition of instillation liquid or blood transfusion liquid.

More particularly, when the liquid flows into the heating bag 26 at a temperature $t_{1a}$, the control circuit 60 calculates, in accordance with the temperature $t_{1a}$ and the predetermined reference temperature $t_s$, a temperature line $L_1$ in FIG. 6 whose rising rate of temperature is constant. Then, the control circuit 60 calculates, according to the temperature line $L_1$, the temperature $t_x$ to which the liquid flowing at the detecting position of the second thermosensor 56 is to have been heated. The control circuit 60 compares the temperature $t_x$ with the actual temperature $t_2$ of the liquid at the detecting position calculated in accordance with the detected signal from the second thermosensor 56; the control circuit 60 transmits a control signal to the first heating plate driving circuit 62 to control the heating operation of the first heating plate 50 in such a manner that, when the temperature $t_2$ is lower than the temperature $t_x$, the heating temperature of the first heating plate 50 is increased, while when the temperature $t_2$ is higher than the temperature $t_x$, the heating temperature of the first heating plate 50 is lowered, until the temperature $t_2$ reaches the temperature $t_x$.

While not shown, the heating device is provided with three devices serving for safety during operation of the heating bag. A first one of these is a thermistor provided adjacent to the third thermosensor 58 and operative at about 42° C. to turn on an emergency lamp. The second one is a temperature control by a thermal relay which is operative at 45° C. The last one is a thermal fuse provided adjacent to the thermosensor 58 and operative at 89° C., when, for example, supply of the liquid is stopped, for disconnecting the instrument from the power supply to completely stop the function of the instrument.

The heating device described above is operated as follows. The instillation liquid or blood transfusion liquid introduced through the inlet pipe 28 of the heating bag 26 flows down in a zigzag way along the passage 34 of the heating bag 26, heated by the first and second heating plates 50 and 52, and is led out through the outlet pipe 30. The electronic control circuit 60 calculates the temperature $t_1$ of the introduced liquid in accordance with the detected signal from the first thermosensor 54, the temperature $t_2$ of the liquid heated by the first heating plate 50 in accordance with the detected signal from the second thermosensor 56 and the temperature $t_3$ of the liquid led out through the outlet pipe 30 in accordance with the detected signal from the third thermosensor 58. The control circuit 60 calculates, in accordance with the temperature $t_1$ and the predetermined reference temperature $t_s$, the temperature line L whose rising rate of temperature is constant, and then calculates the temperature $t_x$ to which the liquid flowing at the detecting position of the second thermosensor 56 is to have been heated. Now, the control circuit 60 compares the temperature $t_x$ with the actual temperature $t_2$ of the liquid at the detecting position calculated in accordance with the detected signal from the second thermosensor 56; the control circuit 60 transmits a control signal to the first heating plate driving circuit 62 to control the heating operation of the first heating plate 50 in such a manner that, when the temperature $t_2$ is lower than the temperature $t_x$, the heating temperature of the first heating plate 50 is increased, while when the temperature $t_2$ is higher than the temperature $t_x$, the heating temperature of the first heating plate 50 is lowered, until the temperature $t_2$ reaches the temperature $t_x$. At the same time, the control circuit 60 compares the temperature $t_3$ with the reference temperature $t_s$ (36° C.) and transmits a control signal to the second heating plate driving circuit 64 to control the heating operation of the second heating plate 52, so that the temperature $t_3$ will reach the reference temperature $t_s$, in the same way as that for the first heating plate 50.

The above control system may include an additional program for controlling the heating rate of the second heating plate 52 in accordance with the rising rate of the liquid temperature obtained by the first heating plate 50. In this case, if the result of rise of the liquid temperature obtained by applying electric power $W_1$ to the first heating plate 50 is $\Delta t_1$, the power to be applied to the second heating plate 52 is represented by the following formula: $k\ (t_s-t_2)/\Delta t_1 \times W_1$, where k is a coefficient defined by, such as, the length of the passage 34 contacting the heating plates, and can be previously determined. Thus, the second heating plate 52 is controlled in consideration with all influences such as of the flow rate and specific heat of the liquid and room temperature, the temperature $t_3$ being expected to become almost equal to the reference temperature $t_s$. Therefore, feedback between the temperatures $t_s$ and $t_3$ is effected only when the temperature $t_3$ will not become equal to $t_s$ under specific circumferences, and the temperature of the liquid flowing out of the device can be adjusted within a quite limited range of temperature.

According to the process described above, as the liquid introduced into the heating bag 26 is heated under control along the temperature line L, the liquid can be positively heated to the reference temperature $t_s$ at a stable rising rate of temperature without any heating fluctuation, instantly responsible to variations in temperature of the introduced liquid. Furthermore, the stable heating control causes less power consumption of the heating plates.

Figure 7:
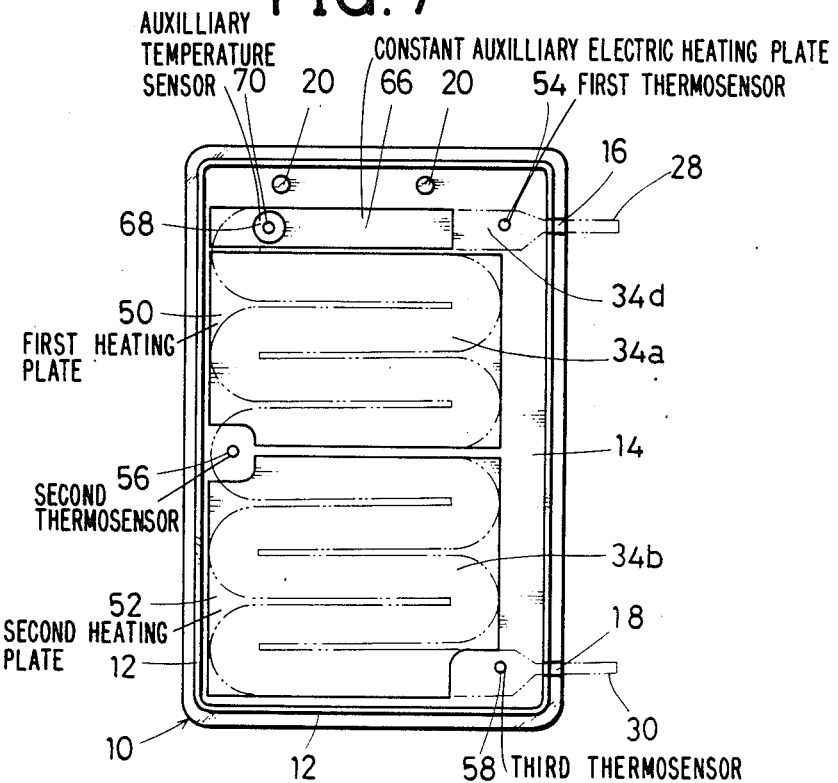
FIG. 7 is a top plan view of the heating device incorporating another embodiment of the present invention.

FIG. 7 is a plan view of the heating bag storing compartment according to another embodiment of the present invention. As shown therein, the casing 10 has in the vicinity of the first heating plate 50 an auxiliary heating plate 66 for heating the first linear portion 34d of the passage 34 of the heating bag 26 extending from the inlet pipe 28 thereof. The auxiliary heating plate 66 is provided with an auxiliary thermosensor 70 surrounded by a heat insulator 68 positioned at a certain distance apart from the first thermosensor 54. The auxiliary heating plate 66 is constructed such as to heat the linear portion 34d of the passage 34 of the heating bag 26 always at a constant heating rate. With this arrangement, therefore, when the flow rate of the liquid is small, a high temperature is detected by the auxiliary thermosensor 70 and, as the flow rate increases, the detected temperature is lowered. Thus, in this embodiment heating rates of the heating plates are controlled also by using the flow rate of the liquid in accordance with the above principle.

Figure 8:
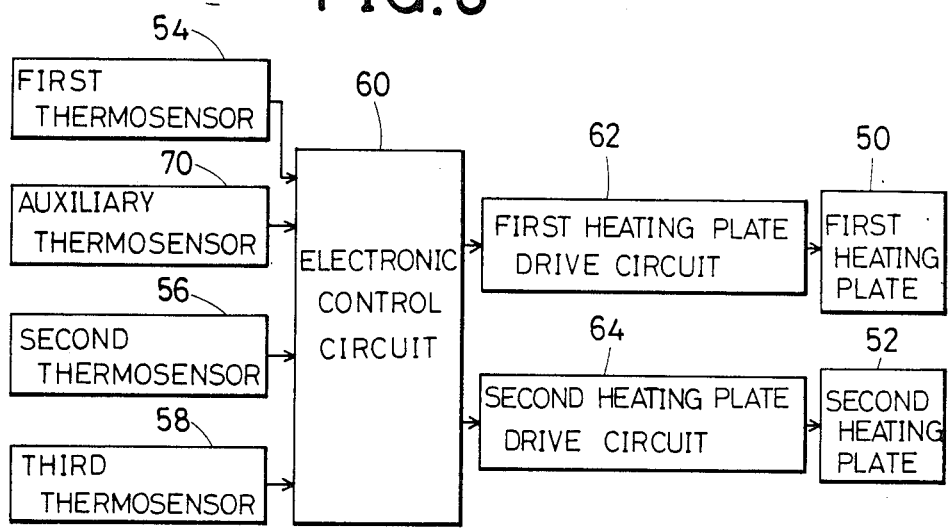
FIG. 8 is a block diagram illustrating the control system for the embodiment shown in FIG. 7.

Now, the control of the heating rate will be described with reference to the block diagram in FIG. 8. The control circuit 60 receives the signals detected by the first, second and third thermosensors 54, 56 and 58, and further a temperature signal fed from the auxiliary thermosensor 70. The control circuit 60 calculates a desired temperature $t_x$ at the detecting position of the second thermosensor 56 in accordance with the detected temperature $t_1$ and the predetermined reference temperature $t_s$. The desired temperature $t_x$ is compared with the temperature detected by the first thermosensor 54, and the compared value is multiplied by the flow rate of the liquid calculated in accordance with the temperature difference between the first thermosensor 54 and the auxiliary thermosensor 70 to thereby calculate a required heating rate. In accordance with the calculated value, the control circuit 60 transmits a control signal to the first heating plate driving circuit 62 to control the heating rate of the first heating plate 50. In the same way, the reference temperature $t_s$ is compared with the temperature detected by the second thermosensor 56, and the compared value is multiplied by the flow rate of the liquid calculated in accordance with the temperature difference between the first thermosensor 54 and the auxiliary thermosensor 70 to thereby calculate a heating rate required for the second heating plate 52. In accordance with the calculated value, the control circuit 60 transmits a control signal to the second heating plate driving circuit 64 to control the heating rate of the second heating plate 52. Therefore, not only the temperature but also the flow rate of the liquid flowing into the heating bag 26 are detected and the heating rates of the heating plates 50 and 52 are controlled in accordance with the temperature difference and the flow rate, so that accurate control of the liquid temperature can be effected in response to variations in flow rate of the liquid.

In the above described process, the temperature of the liquid flowing out of the device is normally expected to reach the predetermined value $t_s$, but comparison between the temperatures $t_3$ and $t_s$ may be fed back to control the current of the second heating plate driving circuit 64. In normal cases, the feedback will not function, but if any trouble should occur to cause difference between the temperatures $t_3$ and $t_s$, the feed back will function to more positively maintain a constant liquid temperature.

FIG. 9 is a perspective view of the heating device according to a further embodiment of the present invention. The difference in the embodiment of FIG. 9 is that a modified heating plate 71 is provided corresponding to the heating plates 50 and 52 described above but having ridges 72 formed thereon. It will be appreciated that when liquid is supplied into the passage 34 of the heating bag 26, the section of the liquid passage forms itself into a downwardly expanded shape, as shown in FIG. 12, due to weight and pressure of the liquid, the upper portion of the passage being extremely restricted. Then, bubbles tend to be produced in the liquid, and will remain in the passage 34, reducing the efficiency of liquid heating operation and yet causing inaccurate control of the heating rate. In this embodiment, a modified heating plate 71 is provided having ridges 72 on the surface thereof. Each of the ridges 72 has a wedge-shaped section with an inclined surface protruding downwardly (considered when in use). As may be seen in FIG. 10, the ridges 72 extend alternately from either side of the heating bag storing compartment 14 toward the center thereof in such a manner that, when the heating bag 26 is placed in the heating bag storing compartment 14, they are positioned on the lower half part of each of rightward and leftward portions of the liquid passage 34 extending in a zigzag way. Also, the push plate 42 is formed on the surface thereof with similar ridges 74, which are disposed in such a manner that, when the heating bag 26 is held between the heating plates 50 and 52 and the push plate 42, the ridges 74 are positioned on the lower half of each of the rightward and leftward portions of the passage 34 extending in a zigzag way in opposing relationship with the ridges 72 of the heating plate 71.

When liquid flows into the heating bag 26 held in the heating device thus constructed, each portion of the passage 34 pushed on the lower half side thereof between the ridges 72 of the heating plate 71 and the ridges 74 of the push plate 42 is expanded at the upper half part thereof and tapered to a point at the lower half part, as best shown in FIG. 11. As the result, generation of bubbles is reduced and if any bubbles are generated, they go up in the upper expanded part of the passage 34 to be rapidly ejected out of the heating bag 26.

Figure 13:
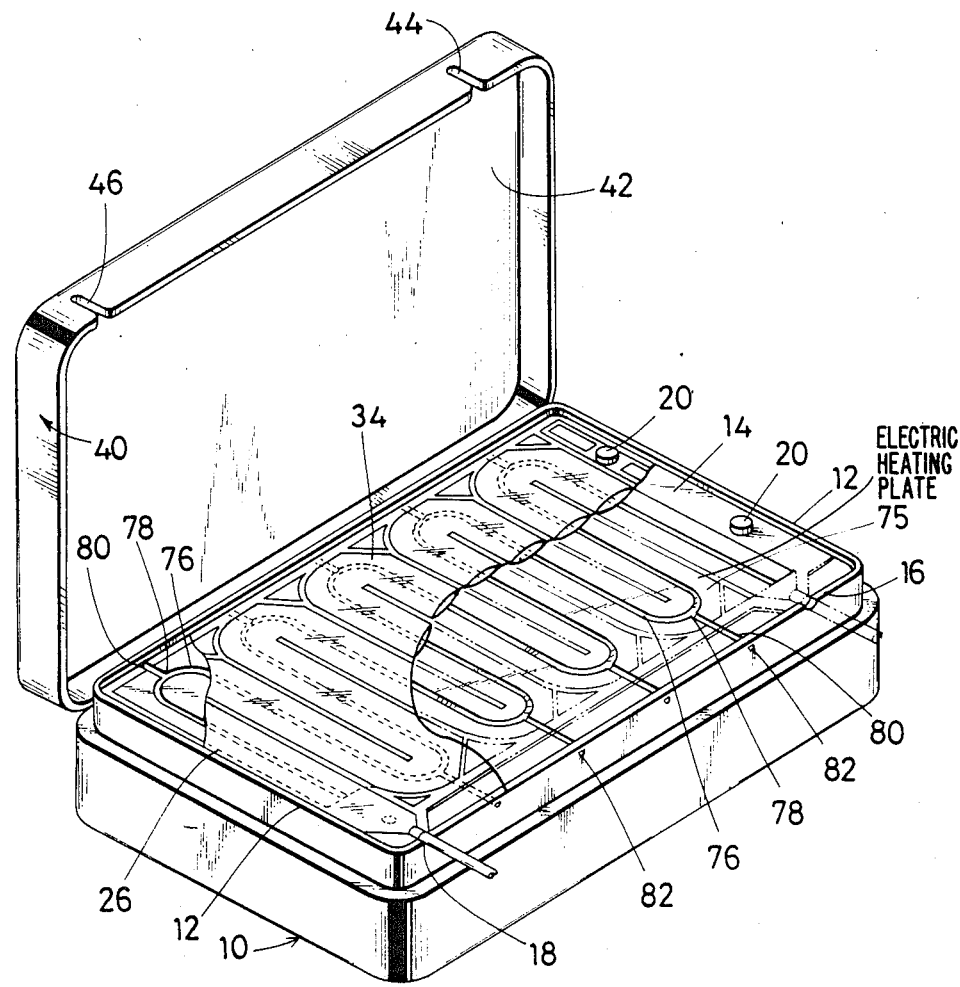
FIG. 13 is a perspective view of the heating device incorporating a still further embodiment of the present invention; and, FIG. 14 is an enlarged fragmentary sectional view of the embodiment shown in FIG. 13.
Figure 14:
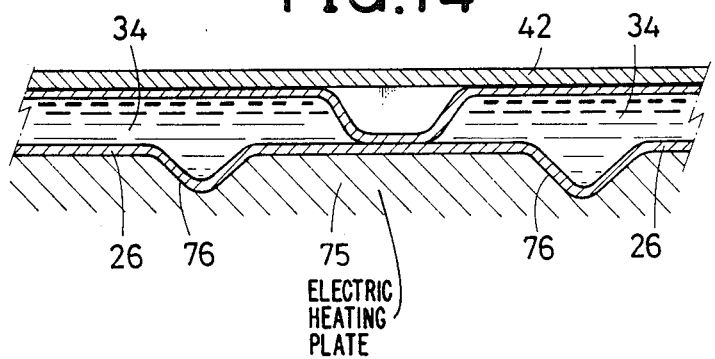

Referring next to FIG. 13, a further embodiment of the present invention is shown. The difference in the embodiment of FIG. 13 is that another modified heating plate 75 is provided corresponding to the heating plates 50 and 52 described above but having a groove 76 formed therein. It will be appreciated that since the heating bag 26 is made of thin plastic films laminated and adhered to each other, some space is created between the heating bag 26 and the heating plates 50 and 52 described above, especially when the heating bag 26 is first placed in the heating bag storing compartment 14. If liquid is supplied into the heating bag 26 in this state, the liquid passage 34 is expanded, but there is no place for air to escape; the air remains between the heating bag 26 and the heating plates 50 and 52, preventing complete contact between the heating bag 26 and the heating plates 50 and 52. In order to meet this problem, in this embodiment, a modified heating plate 75 is provided having a groove 76 extending right and left in a zigzag way along the liquid passage 34. A plurality of extension grooves 80 are connected in air flow communication with the points 78 of arcuate portions, respectively, of the groove 76. The outer ends of the extension grooves 80 are connected to through holes 82 formed in the side wall of the casing 10.

In the embodiment described above, when liquid flows into the passage 34 of the heating bag 26, the air between the heating bag 26 and the heating plate 75 is exhausted through the groove 76, the extension grooves 80 and then the through holes 82, and there remains no air, permitting complete contact between the passage 34 and the heating plate 75. Now, when the passage 34 is expanded due to pressure of the liquid, the portion of the passage 34 abutting on the groove 76 is pressed into the groove 76 and comes in contact with the heating plate 75 for satisfactory heat exchange.

From the foregoing detailed description of the device for heating infusion liquid such as instillation liquid and blood transfusion liquid, it can be seen that the device is very useful in that the heating means can be controlled in accordance with the temperature of the liquid as it flows into the heating device, permitting stable supply of the liquid heated to a predetermined temperature with no heating fluctuation and also reduction of power consumption of the heating means. Furthermore, as the heating rate of the heating plates can be controlled in consideration with not only the temperature of the liquid as it flows into the heating bag but also the flow rate thereof, the room temperature, the specific heat of the liquid and other factors, the device of the invention may accurately control the liquid temperature responsive to the variation in various factors described above. Also, it can be appreciated that the ridges formed on the heating plate and the push plate can effectively prevent deformation of the passage and thence generation of bubbles in the heating bag and permitting rapid ejection of bubbles, if any generated. Furthermore, the grooves formed on the heating plate eliminates the possibility of air remaining between the heating bag and the heating plate, permitting excellent efficiency of heating operation.

The present invention has been described in detail with reference to most preferred embodiments. It is apparent that certain changes and modifications may be made without departing from the spirit and scope of the present invention. It is intended that all matter contained in the above description or shown in the accompanying drawings shall be interpreted as illustrative and not in a limiting sense.

What is claimed is:

1. A device for heating infusion liquid, such as instillation liquid and blood transfusion liquid, to be injected to a human body, comprising:
   a casing having an open top and a closed bottom, with an inlet cutout section and an outlet cutout section formed on one side wall thereof;
   a liquid heating bag removably mounted within said casing and having an inlet end for connection to a source of liquid, an outlet end for connection to a human body, and a flow passage extending between said inlet and outlet ends in a zigzag line, said heating bag being disposed within said casing with said inlet and outlet ends received in said inlet and outlet cutout sections of said casing, respectively;
   a first and a second heating plate mounted on the bottom of said casing, said first heating plate being adapted to heat a half part of the bag on the inlet side of said heating bag, and said second heating plate being adapted to heat the other half part of the bag on the outlet side of said heating bag;
   an openable cover connected to the top of said casing in coextensive relation thereto;
   a push plate mounted on the inner surface of said cover and adapted to hold said heating bag against said first and second heating plates;
   a first thermosensor located within said casing between said inlet cutout section and said first heating plate to measure temperature in the vicinity of the inlet of the bag;
   a second thermosensor located within said casing between said first heating plate and said second heating plate to measure temperature in the vicinity of the middle of the bag;
   a third thermosensor located within said casing between said second heating plate and said outlet cutout section to measure temperature in the vicinity of the outlet of the bag; and
   control means located within said casing for controlling heating rates of said first and second heating plates, said control means including means for controlling said first heating plate in accordance with the temperature of the liquid in the vicinity of the inlet of the bag and the middle of the bag, as measured by said first and second thermosensors, respectively, and said control means further including means for controlling said second heating plate in accordance with the temperature of the liquid in the vicinity of the outlet of the bag, as measured by said third thermosensor.

2. The device of claim 1, wherein said casing supports said heating plates and said heating bag in a substantially vertical orientation during use, said heating plates being in a substantially vertical plane with said first heating plate above said second heating plate, and said inlet end being above said outlet end.

3. The device as defined in claim 2 further comprising an auxiliary heating plate provided adjacent said inlet end, at the upper part, during use, of said first heating plate and adapted for heating a first linear portion of said heating bag at a constant heating rate, an auxiliary thermosensor for detecting the temperature of the liquid heated by said auxiliary heating plate, said auxiliary heating plate and said auxiliary thermosensor defining a means for detecting the flow rate of the liquid, and said control means including means for controlling the heating rate of said first heating plate in accordance with the temperature detected by said first and second thermosensors and the flow rate of the liquid detected by said flow rate detecting means, and said second heating plate in accordance with the temperature detected by said third thermosensor and the flow rate of the liquid detected by said flow rate detecting means.

4. A device for heating infusion liquid such as instillation liquid and blood transfusion liquid to be injected to a human body, comprising:
   a casing having an open top and a closed bottom, said casing having an inlet cutout section and an outlet cutout section formed on one side wall thereof and having a plurality of through holes formed in the opposite side walls thereof;
   a liquid heating bag removably mounted within said casing and having an inlet end for connection to a source of liquid, an outlet end for connection to a human body, and a flow passage extending between said inlet and outlet ends in a zigzag line, said heating bag being disposed within said casing with said inlet and outlet ends received in said inlet and outlet cutout sections of said casing, respectively;
   a heating plate mounted on the bottom of said casing and having a groove formed thereon along the portion contacting the liquid passage of said heating bag, said groove having extension ends defining passages connected in air flow communication with said through holes of said casing, said groove and extension ends serving to evacuate air between said heating bag and said heating plate, for improving heat exchange therebetween;
   an openable cover connected to the top of said casing in coextensive relation thereto; and
   a push plate mounted on the inner surface of said cover and adapted to hold said heating bag against said heating plates.

5. A device for heating infusion liquid, such as instillation liquid and blood transfusion liquid, to be injected to a human body, comprising:
   a casing having an open top and a closed bottom, with an inlet cutout section and an outlet cutout section formed on one side wall thereof;
   a liquid heating bag removably mounted within said casing and having an inlet end for connection to a source of liquid, an outlet end for connection to a human body, and a flow passage extending between said inlet and outlet ends in a zigzag line, said heating bag being disposed within said casing with said inlet and outlet ends received in said inlet and outlet cutout sections of said casing, respectively;
   a heating plate mounted on the bottom of said casing;
   an openable cover connected to the top of said casing in coextensive relation thereto; and
   a push plate mounted on the inner surface of said cover and adapted to hold said heating bag against said heating plate;
   said casing supporting said heating bag and said heating plate in a substantially vertical orientation during use, with said inlet end above said outlet end;
   said heating plate and said push plate being formed on their opposed surfaces with ridges having a wedge shape, each of said ridges having an inclined surface protruding, during use, downwardly and inwardly toward said heating bag, the ridges on said heating plate and said push plate causing deformation of the flow passage of said heating bag mounted therebetween, the passage assuming a shape in cross section, during use, having a greater thickness at its upper portions.

* * * * *